(12) United States Patent
Lee et al.

(10) Patent No.: US 8,568,329 B2
(45) Date of Patent: Oct. 29, 2013

(54) BASELINE DRIFT CANCELING METHOD AND DEVICE

(75) Inventors: Shiow-Harn Lee, Hsinchu (TW); Wen-Yang Chou, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 678 days.

(21) Appl. No.: 12/484,092

(22) Filed: Jun. 12, 2009

(65) Prior Publication Data

US 2010/0168595 A1     Jul. 1, 2010

(30) Foreign Application Priority Data

Dec. 31, 2008 (TW) .............................. 97151767 A

(51) Int. Cl.
*A61B 5/02* (2006.01)
(52) U.S. Cl.
USPC .......................................................... 600/508
(58) Field of Classification Search
USPC .................................................. 600/508–509
See application file for complete search history.

(56) References Cited

U.S. PATENT DOCUMENTS

| | | | |
|---|---|---|---|
| 5,107,849 A * | 4/1992 | Bellin et al. ................... | 600/508 |
| 5,269,313 A | 12/1993 | DePinto | |
| 5,318,036 A | 6/1994 | Arand et al. | |
| 5,762,068 A * | 6/1998 | dePinto .......................... | 600/509 |
| 5,772,603 A * | 6/1998 | Ohlsson et al. ................ | 600/509 |
| 5,999,845 A * | 12/1999 | dePinto .......................... | 600/509 |
| 6,280,391 B1 | 8/2001 | Olson et al. | |
| 6,496,721 B1 * | 12/2002 | Yonce ............................. | 600/509 |
| 6,881,191 B2 | 4/2005 | Oakley et al. | |
| 2007/0078354 A1 | 4/2007 | Holland | |
| 2007/0173734 A1 | 7/2007 | Kim et al. | |

FOREIGN PATENT DOCUMENTS

| | | |
|---|---|---|
| TW | 1222861 | 11/2004 |
| TW | 1272090 | 2/2007 |
| TW | 200824650 | 6/2008 |

OTHER PUBLICATIONS

V.S. Chouhand et al. "Total Removal of Baseline Drift from ECG Signal," Proceedings of the International Conference on Computing: Theory and Applications, 4 pages, Mar. 2007, US.
R.F. von Borries et al. "Wavelet Transform-Based ECG Baseline Drift Removal for Body Surface Potential Mapping," Proceedings of the 2005 IEEE Engineering in Medicine and Biology 27th Annual Conference, pp. 3891-3894, Sep. 2005, Shanghai, China.
Taiwan Patent Office, Office Action, Application Patent Serial No. 97151767, Apr. 16, 2012, Taiwan.
E. Kaniusas et al., "Embedded Elettrocardiographic Amplifier without reference electrode," International Workshop on Intelligent Solutions in Embedded Systems, 2006, pp. 1-7.

\* cited by examiner

*Primary Examiner* — Amanda Patton

(57) ABSTRACT

An embodiment of a baseline drift canceling method is provided. The method removes a baseline drift signal from a bioelectric signal, and includes the steps as follows: delaying the bioelectric signal by an analog time delay circuit to generate a first bioelectric signal; according to the bioelectric signal to generate a baseline drift signal; and acquiring a second bioelectric signal according to the first bioelectric signal and the baseline drift signal.

21 Claims, 5 Drawing Sheets

BASELINE DRIFT CANCELING METHOD AND DEVICE

CROSS REFERENCE TO RELATED APPLICATIONS

This Application claims priority of Taiwan Patent Application No. 97151767, filed on Dec. 31, 2008, the entirety of which is incorporated by reference herein.

BACKGROUND OF THE INVENTION

1. Field of the Invention

The invention relates to a baseline drift canceling method to remove a baseline drift signal in a bioelectric signal.

2. Description of the Related Art

When measuring the bioelectric signal of a human body, two sensor patches are usually applied for sensation of the human body. Take the electrocardiograph machine for example, the electrocardiograph machine senses the bioelectric signal from sensor patches on the chest or hands of the human body. However, the sensed bioelectric signal is easily affected by the breathing, movement, skin resistance or sweat on the skin of the human body. This may cause the baseline to drift or wander and when the baseline drift is too large, a resulting output signal may be saturated and the bioelectric signal would be inaccurate.

One conventional method to solve the issue of a baseline drift is to directly filter out the baseline drift signal, such as that disclosed in U.S. Pat. No. 5,318,036. The method disclosed by U.S. Pat. No. 5,318,036 filters an output from a front-end filter by a digital high pass filter in a microprocessor to remove the baseline drift. Another conventional method estimates a baseline drift signal by a microprocessor and subtracts the estimated baseline drift signal from the bioelectric signal. The baseline estimation method is disclosed in U.S. Pat. No. 6,280,391 and U.S. Pub. No. 20070078354. Another baseline estimation method is disclosed in U.S. Pat. No. 6,881,191 to estimate the baseline drift signal by curve fitting. However, the described baseline drift canceling methods require complicated circuitry or increased hardware and/or software, thus, delaying results. Additionally, in certain cases, the baseline drift tolerance (the voltage range of the baseline drift/the amplitude of vibration of signal) for the described baseline drift canceling methods are limited.

BRIEF SUMMARY OF THE INVENTION

To solve the described issue, one embodiment of the invention provides a baseline drift canceling method.

An embodiment of a baseline drift canceling method is provided. The method removes a baseline drift signal in a bioelectric signal, and comprises the steps as follows: delaying the bioelectric signal by an analog time delay circuit to generate a first bioelectric signal; according to the bioelectric signal to generate a baseline drift signal; and acquiring a second bioelectric signal according to the first bioelectric signal and the baseline drift signal.

An embodiment of a baseline drift canceling device is provided to remove a baseline drift signal in a bioelectric signal. The baseline drift canceling device comprises a first amplifier, a baseline drift canceling unit and a digital amplifier. The first amplifier receives and amplifies a sensing signal to generate the bioelectric signal. The baseline drift canceling unit comprises a low pass filter, an analog time delay circuit and an adder. The low pass filter receives the bioelectric signal to generate the baseline drift signal. The analog time delay circuit delays the bioelectric signal to generate a first bioelectric signal. The adder receives the baseline drift signal and the first bioelectric signal to generate a second bioelectric signal. The digital amplifier receives and amplifies the second bioelectric signal to generate a digital bioelectric signal.

Another embodiment of a bioelectric signal sensing apparatus is provided. The apparatus comprises a first sensor, a second sensor, a first amplifier and at least one baseline drift canceling unit. The first sensor outputs a first sensing signal. The second sensor outputs a second sensing signal. The first amplifier receives the first sensing signal and the second sensing signal to generate a bioelectric signal. The baseline drift canceling unit comprises a low pass filter, an analog time delay circuit and an adder. The low pass filter receives the bioelectric signal to generate the baseline drift signal. The analog time delay circuit delays the bioelectric signal to generate a first bioelectric signal. The adder receives the baseline drift signal and the first bioelectric signal to generate a second bioelectric signal.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
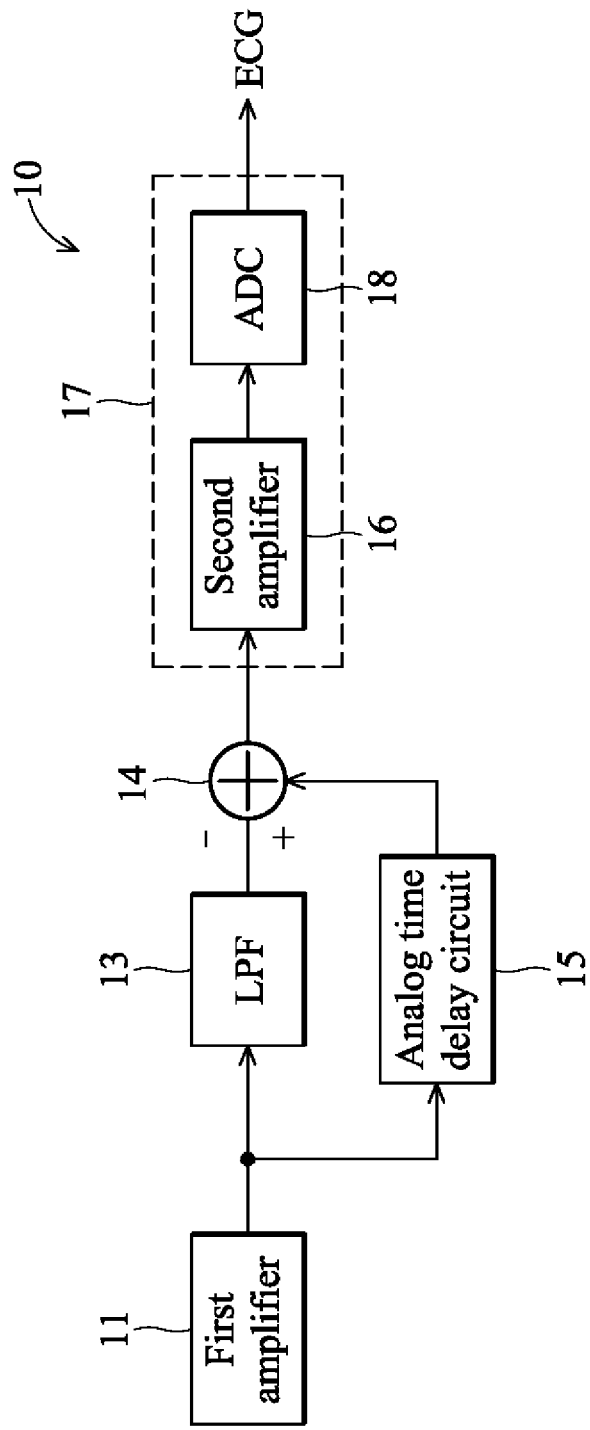
FIG. 1 is a schematic diagram of an embodiment of a baseline drift canceling device for a bioelectric signal according to the invention.

FIG. 1 is a schematic diagram of an embodiment of a baseline drift canceling device for a bioelectric signal according to the invention. The baseline drift canceling device 10 comprises a first amplifier 11, baseline drift canceling unit and digital amplifier 17. The baseline drift canceling unit comprises a low pass filter (LPF) 13, an adder 14 and an analog time delay circuit 15. The digital amplifier 17 further comprises a second amplifier 16 and an analog to digital converter (ADC) 18. The first amplifier 11 receives and amplifies a sensing signal to generate a bioelectric signal, and the bioelectric signal is transmitted to the baseline drift canceling unit, i.e., the bioelectric signal is transmitted to both the low pass filter 13 and analog time delay circuit 15. The low pass filter 13 low-pass filters the received bioelectric signal to estimate a baseline drift (BLD) signal.

The analog time delay circuit 15 delays the received bioelectric signal for a predetermined time to generate a first bioelectric signal, and the predetermined time varies according to the processing time of the low pass filter 13. In other words, the output of the analog time delay circuit 15 synchronizes with the output of the low pass filter 13. The adder 14 comprises a non-inverting input terminal (+) and an inverting input terminal (−) which respectively receives the first bioelectric signal from the analog time delay circuit 15 and the estimated baseline drift signal from low pass filter 13. The adder 14 subtracts the estimated baseline drift signal from the first bioelectric signal to generate a second bioelectric signal. The digital amplifier 17 receives and amplifies the second bioelectric signal output by the adder 14 to generate a digital bioelectric signal, wherein the second amplifier 16 amplifies the second bioelectric signal and the analog to digital converter 18 converts the second bioelectric signal into the digital bioelectric signal.

In this embodiment, the bioelectric signal is illustrated as an electrocardiography (ECG) signal, but the invention is not limited thereto. In another embodiment, the bioelectric signal may be an electroencephalogram (EEG) signal, an electromyogram (EMG) signal or an electric ocular graph (EOG) signal.

Figure 2:
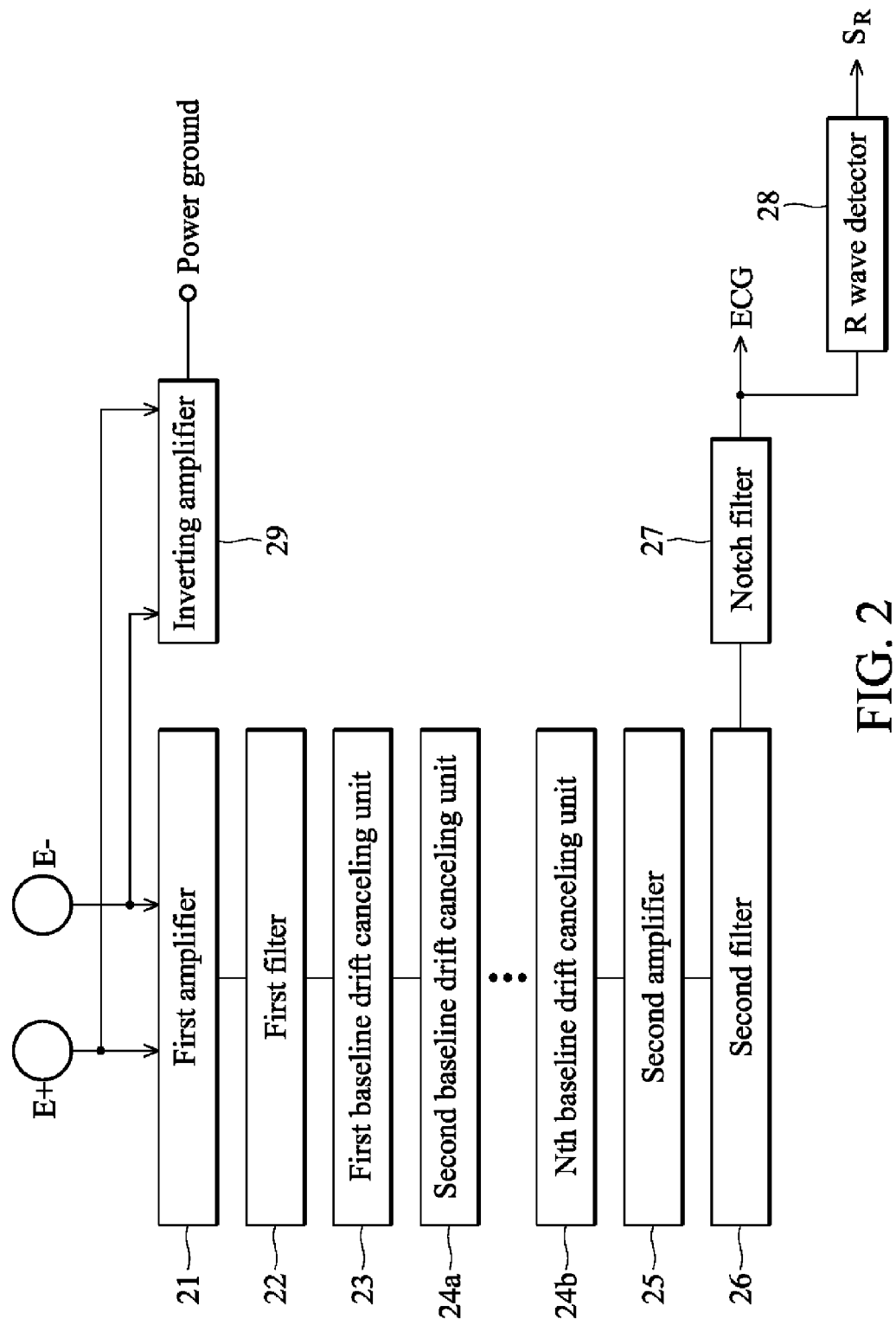
FIG. 2 is a schematic diagram of another embodiment of a baseline drift canceling device for a bioelectric signal according to the invention.

FIG. 2 is a schematic diagram of another embodiment of a baseline drift canceling device for a bioelectric signal according to the invention. The embodiment is illustrated as an electrocardiography (ECG) signal, but the invention is not limited thereto. The first amplifier 21 receives and amplifies two sensing signals from the bioelectricity sensors E+ and E− to generate an ECG signal. The bioelectricity sensors E+ and E− directly contact with the body of a patient. Since a voltage difference between the body of the patient and a ground voltage level exists, an inverting amplifier 29 is used to eliminate the voltage difference. In other words, the inverting amplifier 29 is used to reduce the common mode voltage. In another embodiment, the inverting amplifier 29 is further coupled to a filter.

The first filter 22 filters the ECG signal from the first amplifier 21. Then, the filtered ECG signal is processed by the first baseline drift canceling unit 23, the second baseline drift canceling unit 24a and the Nth baseline drift canceling unit 24b to remove the baseline drift from the ECG signal. In this embodiment, the number of baseline drift canceling units is not limit to the number shown in FIG. 2. Those skilled in the art can use more baseline drift canceling units for a smooth ECG signal according to the baseline drift in the ECG signal. The second amplifier 25 receives and amplifies the processed ECG signal from the Nth baseline drift canceling unit 24b. The second filter 26 filters the ECG signal from the second amplifier 25. In this embodiment, the first filter 22 is a high pass filter, such as a high pass filter with high common mode rejection ration. The second filter 26 is a low pass filter. In this embodiment, the gain of the first amplifier 21 is about 5-10, and the gain of the second amplifier 25 is about 100.

The notch filter 27 receives a signal from the second filter 26 and eliminates the frequency interference therein, wherein the frequency interference is caused by 50 Hz or 60 Hz alternating current (AC) power. The smooth ECG signal output by the notch filter 27 is transmitted to the R wave detector 28 to generate a heartbeat pulse signal $S_R$. In this embodiment, it is illustrated as only one notch filter, but it can use more notch filters to eliminate the frequency interference caused by the alternating current frequency. It is noted that the frequency interference which can be eliminated by the notch filter is not limit to the frequency interference of 50 Hz or 60 Hz. In this embodiment, a gain compensation circuit is coupled to the notch filter 27 to adjust the gain of the output of the second filter 26.

Figure 3:
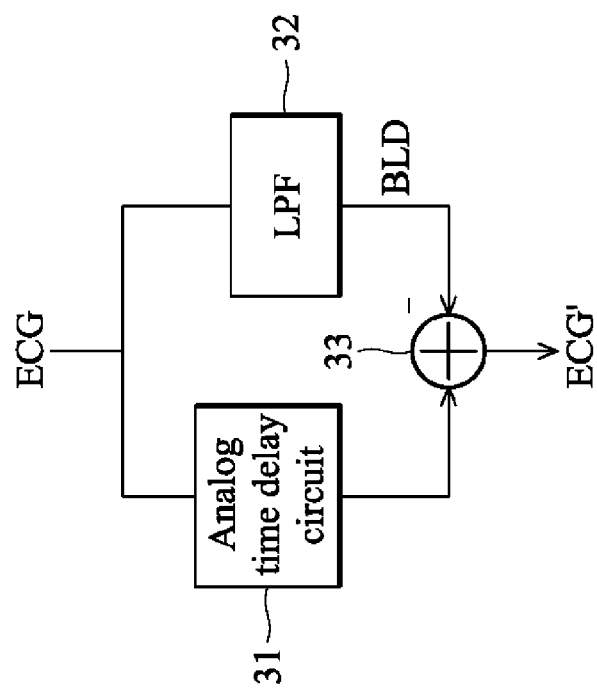
FIG. 3 is a schematic diagram of an embodiment of a baseline drift canceling unit according to the invention.

FIG. 3 is a schematic diagram of an embodiment of a baseline drift canceling unit according to the invention. The ECG signal is transmitted to a low pass filter 32 and an analog time delay circuit 31. The low pass filter 32 filters the ECG signal to estimate a baseline drift (BLD) signal.

The analog time delay circuit 31 delays the received ECG signal for a predetermined time, wherein the predetermined time varies according to the processing time of the low pass filter 32. In other words, the output of the analog time delay circuit 31 synchronizes with the output of the low pass filter 32. The adder 33 comprises a non-inverting input terminal (+) and an inverting input terminal (−) which respectively receives the output signal from the analog time delay circuit 31 and the output signal from low pass filter 32. The adder 33 subtracts the estimated baseline drift signal from the output signal of the analog time delay circuit 31 to generate a bioelectric signal ECG'. In another embodiment, the adder 33 can be replaced by a subtractor.

Figure 4:
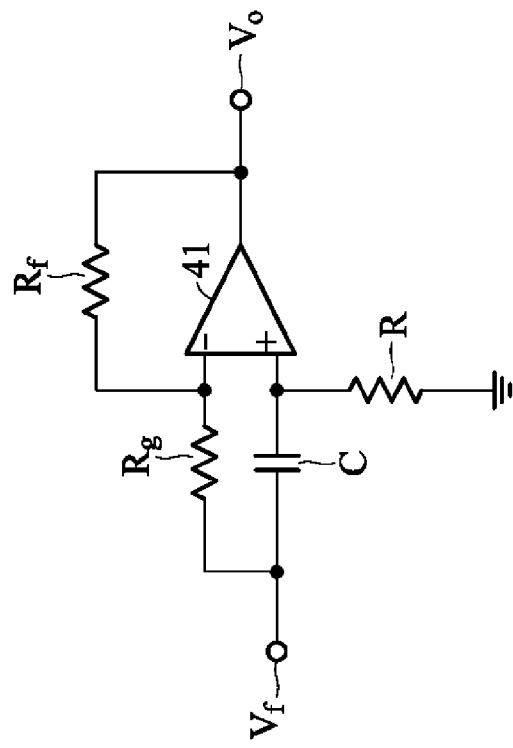
FIG. 4 is a schematic diagram of an embodiment of an analog time delay circuit according to the invention

FIG. 4 is a schematic diagram of an embodiment of an analog time delay circuit according to the invention. The analog time delay circuit is made up of an operational amplifier 41, resistors R, $R_g$, $R_f$ and a capacitor C. Resistors $R_g$ and $R_f$ determine the gain. Resistor R and capacitor C determines the delay time. The mathematical equation of the delay time can be expressed as follows:

$$\frac{V_O}{V_i} = \exp(-\tau S).$$

When τ S is much smaller than 1, the equation can be approximated as the following:

$$\frac{V_O}{V_i} = \exp(-\tau S) \approx \frac{1 - \frac{\tau S}{2}}{1 + \frac{\tau S}{2}} = \frac{1 - R \cdot C \cdot S}{1 + R \cdot C \cdot S}.$$

Therefore, the delay time or phase lag derived from the inverting amplifier and the delay time of the low pass filter can be estimated and the resistance of resistor R and capacitance of capacitor C according to the described equation can be determined. Then, the corresponding analog time delay circuit can be implemented.

Figure 5:
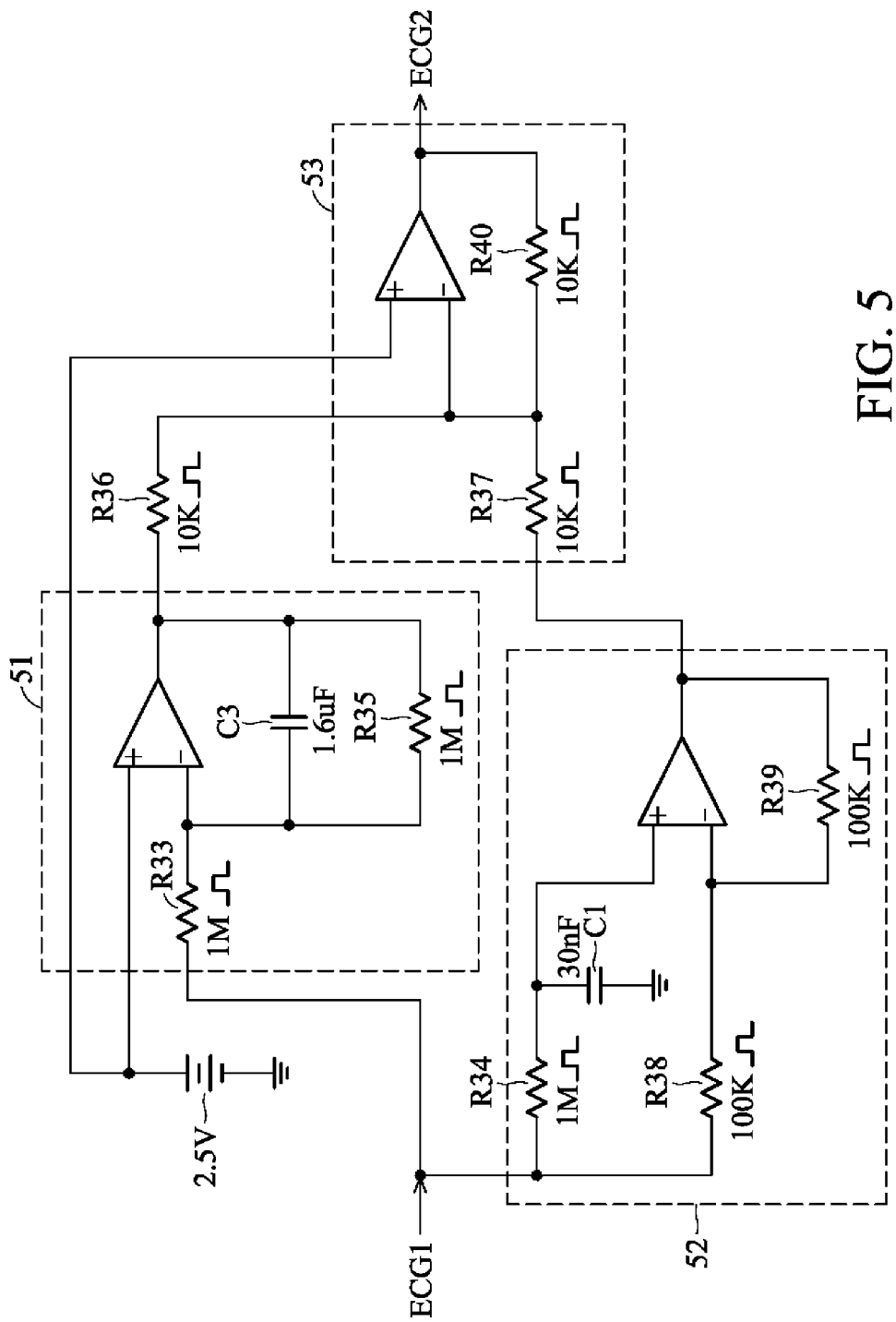
FIG. 5 is a schematic diagram of another embodiment of a baseline drift canceling unit according to the invention.

FIG. 5 is a schematic diagram of another embodiment of a baseline drift canceling unit according to the invention. The detailed circuitry of a low pass filter 51, an analog time delay circuit 52 and an analog adder 53 is shown in FIG. 5. In this embodiment, the 3 dB frequency of the low pass filter 51 is 1 Hz. In another embodiment, the 3 dB frequency of the low pass filter 51 can be between 0.5 Hz to 1 Hz by adjusting the capacitance of the capacitor C3 and the resistance of resistor $R_{35}$. In FIG. 5, a time constant corresponding to the 3 dB frequency of the low pass filter 51 is between 2 seconds and 1 second, a time constant of the analog time delay circuit 52 corresponding to the 3 dB frequency of the low pass filter 51 is between 90 milliseconds and 50 millisecond, and a compensation gain of the low pass filter 51 and the adder 53 corresponding to the 3 dB frequency of the low pass filter 51 is between 1.25 and 1.05.

Figure 6:
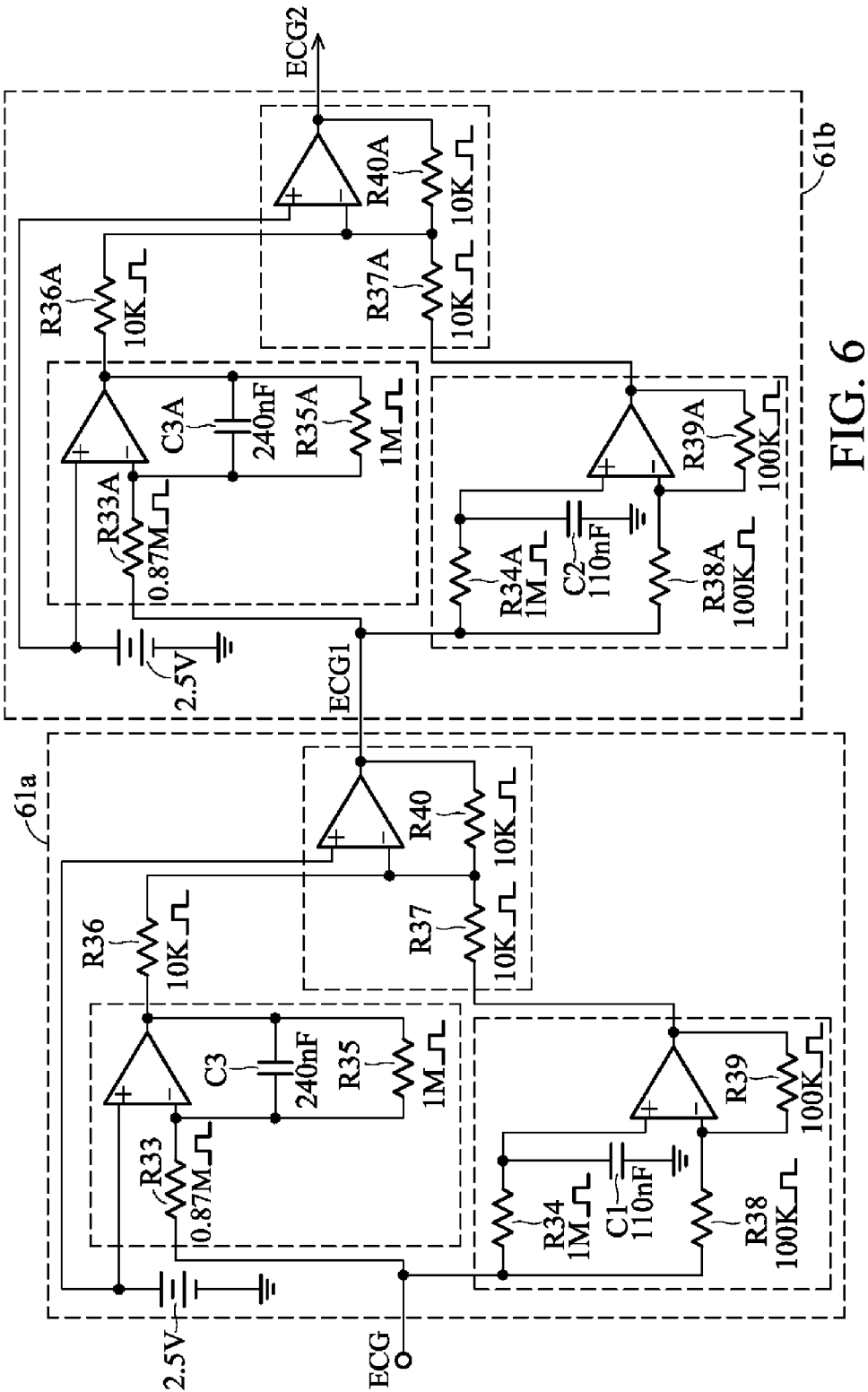
FIG. 6 is a schematic diagram of another embodiment of two cascaded baseline drift canceling units according to the invention.

FIG. 6 is a schematic diagram of another embodiment of two cascaded baseline drift canceling units according to the invention. In this embodiment, the baseline drift canceling units 61a and 61b eliminate the baseline drift in the ECG signal. In this embodiment, the 3 dB frequency of the low pass filters in both baseline drift canceling units 61a and 61b is 0.67 Hz.

According to the above description, the disclosed baseline drift canceling method removes the baseline drift signal during the front-end filtering process and accordingly the baseline drift tolerance can be also increased. In a conventional baseline drift canceling method, the bioelectric signal is amplified by a first amplifier and a digital amplifier during the front-end filtering operation, and the baseline drift signal is removed from the amplified bioelectric signal during the back-end operation. This may cause the baseline drift signal to be too large and exceed the output range, thus causing error. According to the disclosed baseline drift canceling method, the baseline drift canceling procedure is applied to the bioelectric signal after the bioelectric signal is amplified by a first amplifier, thus baseline drift tolerance is efficiently increased.

Please refer to FIG. 1. Assuming the gain of the first amplifier 11 is 5, the gain of second amplifier 16 is 100, the circuit outputting the ECG signal is powered by a single one power source (5V), the operative voltage of the circuit is from 0.25V to 4.75V and the magnitude of the ECG signal is 0.5V, after the ECG signal is filtered in the front-end filter, the maximum variation of the baseline drift signal is 4V. If the ECG signal input to the second amplifier 16 is 5 mV (5V/100), and the maximum variation of the baseline drift signal is 4.5V. In other word, the ECG signal input to the first amplifier 11 is 1 mV (5 mV/5), and the maximum variation of the baseline drift signal is 0.9V (4.5V/5). Thus, according to the described baseline drift canceling method, the baseline drift tolerance is 900 (0.9V/1 mV). Compared with the convention baseline drift tolerance (4V/0.5V=8), the baseline drift tolerance is significantly increased.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A baseline drift canceling method to remove a baseline drift signal in a bioelectric signal, comprising:
    delaying the bioelectric signal by an analog time delay circuit to generate a first bioelectric signal;
    generating a baseline drift signal according to the bioelectric signal, wherein the baseline drift signal is generated by a low pass filter; and
    acquiring a second bioelectric signal according to the first bioelectric signal and the baseline drift signal.

2. The method as claimed in claim 1, wherein the second bioelectric signal is acquired by subtracting the baseline drift signal from the first bioelectric signal.

3. The method as claimed in claim 1, wherein a delay time of the analog time delay circuit is determined according to a processing time of the low pass filter.

4. The method as claimed in claim 1, further comprising:
    generating a heartbeat pulse signal according to the second bioelectric signal.

5. The method as claimed in claim 1, further comprising:
    receiving a sensing signal by an analog amplifier;
    amplifying the sensing signal by the analog amplifier to generate the bioelectric signal; and
    transmitting the amplified bioelectric signal directly to the low pass filter.

6. A baseline drift canceling device to remove a baseline drift signal in a bioelectric signal, comprising:
    a first amplifier to receive and amplify a sensing signal to generate the bioelectric signal;
    a baseline drift canceling unit, comprising:
        a low pass filter receiving the bioelectric signal directly from the first amplifier to generate the baseline drift signal;
        an analog time delay circuit to delay the bioelectric signal to generate a first bioelectric signal; and
        an adder receiving the baseline drift signal and the first bioelectric signal to generate a second bioelectric signal; and
    a digital amplifier receiving and amplifying the second bioelectric signal to generate a digital bioelectric signal.

7. The device as claimed in claim 6, wherein the 3 dB frequency of the low pass filter is between 0.5 Hz and 1 Hz.

8. The device as claimed in claim 6, wherein a time constant corresponding to the 3 dB frequency of the low pass filter is between 2 seconds and 1 second.

9. The device as claimed in claim 6, wherein a time constant of the analog time delay circuit corresponding to the 3 dB frequency of the low pass filter is between 90 milliseconds and 50 milliseconds.

10. The device as claimed in claim 6, wherein a compensation gain of the low pass filter and the adder corresponding to the 3 dB frequency of the low pass filter is between 1.25 and 1.05.

11. The device as claimed in claim 6, wherein the digital amplifier comprises:
    a second amplifier amplifying the second bioelectric signal; and
    an analog to digital converter converting the second bioelectric signal into the digital bioelectric signal.

12. A bioelectric signal sensing apparatus, comprising:
    a first sensor outputting a first sensing signal;
    a second sensor outputting a second sensing signal;
    a first amplifier receiving the first sensing signal and the second sensing signal to generate a bioelectric signal; and
    at least one baseline drift canceling unit, comprising:
        a low pass filter receiving the bioelectric signal directly from the first amplifier to generate a baseline drift signal;
        an analog time delay circuit to delay the bioelectric signal to generate a first bioelectric signal; and
        an adder receiving the baseline drift signal and the first bioelectric signal to generate a second bioelectric signal.

13. The apparatus as claimed in claim 12, further comprising a notch filter to filter the second bioelectric signal to eliminate an alternating current frequency interference in the second bioelectric signal.

14. The apparatus as claimed in claim 12, wherein the digital amplifier comprises:
    a second amplifier amplifying the second bioelectric signal; and
    an analog to digital converter converting the second bioelectric signal into the digital bioelectric signal.

15. The apparatus as claimed in claim 12, further comprising an inverting amplifier to reduce a common mode voltage.

16. The apparatus as claimed in claim 12, further comprising an R wave detector receiving the second bioelectric signal to generate a heartbeat pulse signal.

17. The apparatus as claimed in claim 12, wherein the bioelectric signal is an electrocardiography signal, an electroencephalogram signal, an electromyogram signal or an electric ocular graph signal.

18. The device as claimed in claim 12, wherein the 3 dB frequency of the low pass filter is between 0.5 Hz and 1 Hz.

19. The apparatus as claimed in claim 12, wherein a time constant corresponding to the 3 dB frequency of the low pass filter is between 2 seconds and 1 second.

20. The apparatus as claimed in claim 12, wherein a time constant of the analog time delay circuit corresponding to the 3 dB frequency of the low pass filter is between 90 milliseconds and 50 millisecond.

21. The apparatus as claimed in claim 12, wherein a compensation gain of the low pass filter and the adder corresponding to the 3 dB frequency of the low pass filter is between 1.25 and 1.05.

* * * * *